United States Patent [19]
Cognard et al.

[11] Patent Number: 5,593,561
[45] Date of Patent: Jan. 14, 1997

[54] MULTIPLE ELECTROPHORESIS METHOD AND APPARATUS FOR MIGRATION AND TRANSFER OF MACROMOLECULES

[75] Inventors: Dominique Cognard, Guyancourt; Jean Hache, Voisin-le-Bretonneux, both of France

[73] Assignee: Bertin & Cie, Plaisir, France

[21] Appl. No.: 464,652

[22] PCT Filed: Dec. 2, 1993

[86] PCT No.: PCT/FR93/01185
  § 371 Date: Jul. 18, 1995
  § 102(e) Date: Jul. 18, 1995

[87] PCT Pub. No.: WO94/14526
  PCT Pub. Date: Jul. 7, 1994

[30] Foreign Application Priority Data
Dec. 22, 1992 [FR] France .................... 92 15451

[51] Int. Cl.⁶ .................................. G01N 27/26
[52] U.S. Cl. ............... 204/456; 204/462; 204/464
[58] Field of Search ............. 204/299 R, 180.1, 204/182.8, 518

[56] References Cited
U.S. PATENT DOCUMENTS
3,888,758  6/1975  Saeed .
4,994,166  2/1991  Fernwood et al. .

FOREIGN PATENT DOCUMENTS
313293      4/1989  European Pat. Off. .
826623      4/1938  France .
WO90/02601  3/1990  WIPO .
WO90/05017  5/1990  WIPO .

Primary Examiner—Donald R. Valentine
Assistant Examiner—Alexander Noguerola
Attorney, Agent, or Firm—Bell, Seltzer, Park & Gibson

[57] ABSTRACT

A multiple electrophoresis method and apparatus for migrating and transferring macromolecules in a vessel (10) containing a plurality of parallel elongate electrodes (14), membranes (22) disposed vertically in the vessel between the columns of electrodes (14), and an electrophoresis gel which is inserted in the vessel in liquid form and which is subsequently solidified to perform electrophoresis. When the electrophoresis is completed, the gel is liquefied, dissolved, or decomposed, and the membranes (22) onto which the macromolecules have been transferred are withdrawn from the vessel.

16 Claims, 2 Drawing Sheets

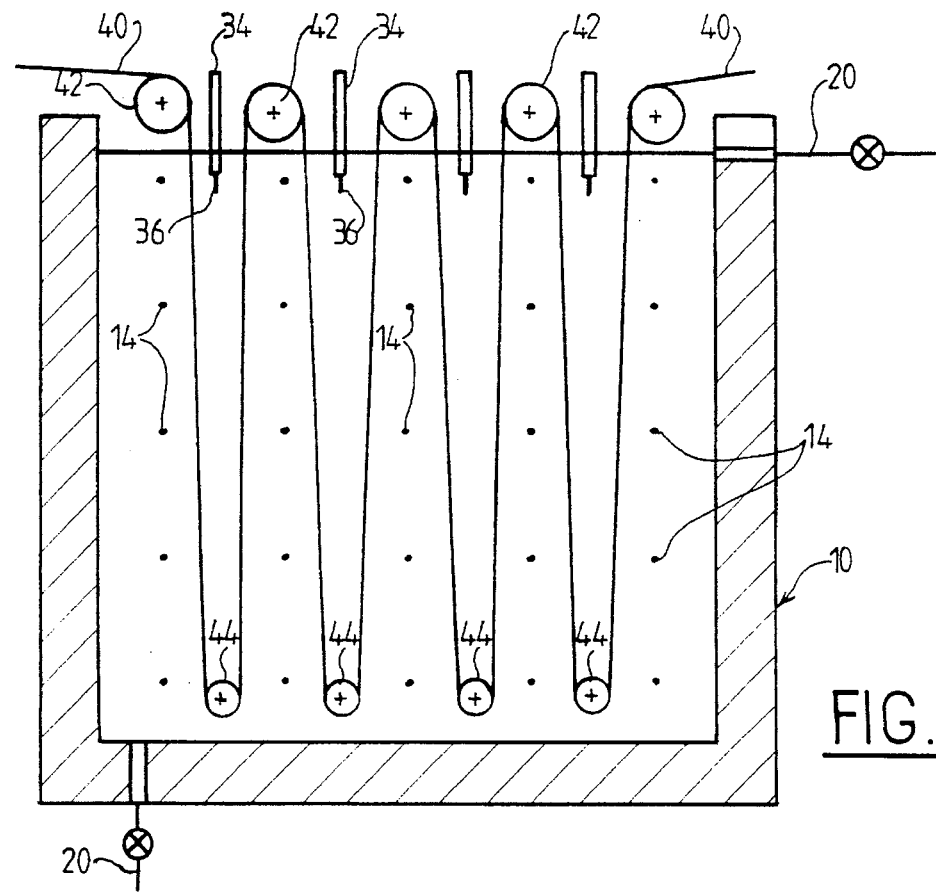
FIG.6
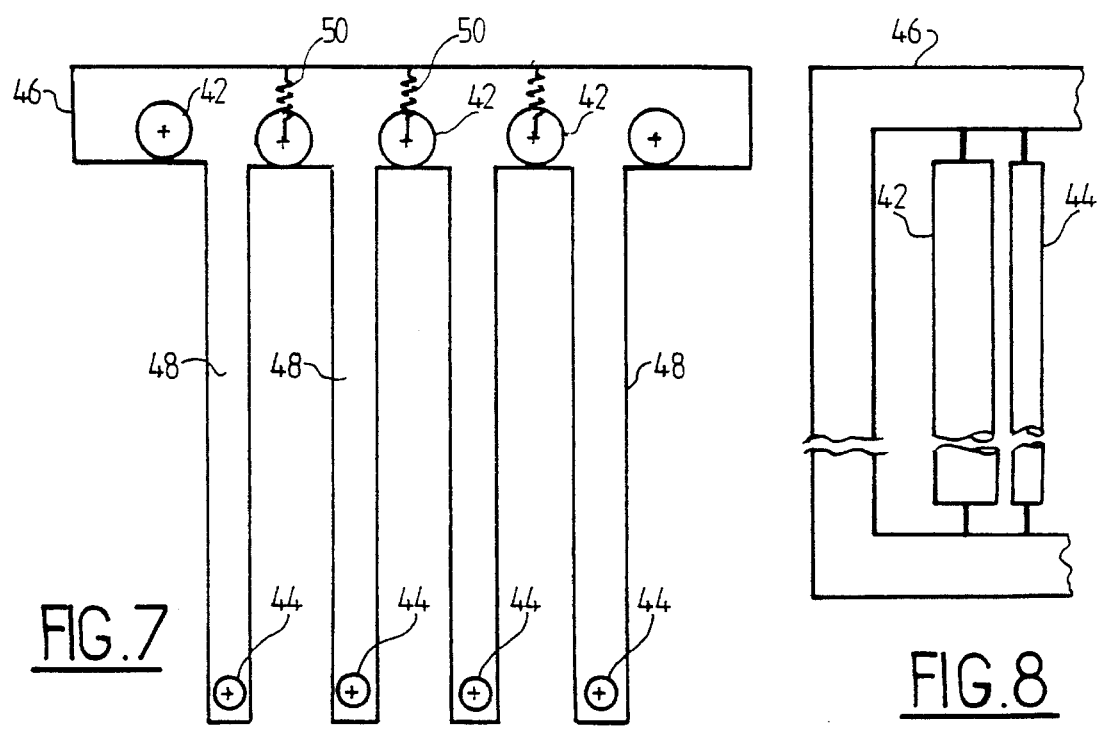
FIG.7
FIG.8

MULTIPLE ELECTROPHORESIS METHOD AND APPARATUS FOR MIGRATION AND TRANSFER OF MACROMOLECULES

The invention relates to a multiple electrophoresis method and apparatus for migration and transfer of macromolecules, such as proteins or nucleic acids.

It is now well known to separate samples of macromolecules by electrophoresis, causing them to migrate through a plate of gel under the effect of an electric field. The samples of macromolecules travel through the gel over distances that are a function of their molecular masses. Under the effect of a second electric field, perpendicular to the first and to the plates of gel, it is possible to transfer the macromolecules onto microporous membranes associated with the plates of gel.

That technique, which was initially lengthy and difficult to implement, has been improved and simplified little by little so that it is now possible to cause macromolecules to migrate and separate and then to transfer them, all within the same vessel and using the same network of electrodes, without any manipulation of the plates of gel or the membranes between migration and transfer of the macromolecules.

In particular, international application WO 90/02601 in the name of the Applicant describes a multiple electrophoresis vessel in which it is possible to place a relatively large number of plates of gel associated with membranes, in order to perform separation and transfer of macromolecules in a manner that is automatic or quasi-automatic. In addition, French patent application 91 08578 in the name of the Applicant describes cassettes for making and manipulating plates of gel associated with membranes, and suitable for use in the electrophoresis vessel described in the above-mentioned international application.

Although those known means have made it possible to achieve results that are quite remarkable, it remains relatively difficult to make up the units each comprising a plate of gel plus a membrane, and special care is required to ensure that the plates of gel are uniform and do not contain bubbles of air, and to ensure that the membranes associated with said plates of gel are thoroughly plane and adhere over their entire working area to the plates of gel. Also, because the gel ages quickly and very poorly, particularly when it is agarose, it is impossible to prepare large quantities of plates of gel with membranes a long time in advance and to store them for subsequent use.

A particular object of the present invention is to provide a solution to the problems that is simple, effective, and cheap.

The invention provides a multiple electrophoresis method and apparatus for separation of macromolecules in gel and transfer thereof onto membranes, but without using prefabricated gel-membrane units.

The invention thus provides a multiple electrophoresis method for controlled migration of macromolecules and transfer thereof onto membranes in a vessel containing a plurality of parallel elongate electrodes and having means for applying electrical potentials to the electrodes for establishing between them successively a first electric field for macromolecule migration, and then a second electric field perpendicular to the first for transferring the macromolecules onto the membranes, the method being characterized in that it consists in placing in the vessel membranes which are parallel to one another and to the electrodes and which extend between the electrodes, and in filling the vessel with an electrophoresis gel in the liquid phase, the filling being performed before or after the membranes have been placed in the vessel, then in solidifying the gel, in subsequently placing samples of macromolecules in wells formed in the gel along one of the edges of the membranes, in applying electrical potentials to the electrodes initially to cause the macromolecules to migrate through the gel, and then to transfer them onto the membranes, then in liquefying, dissolving, or decomposing the gel, and in removing the membranes from the vessel.

The invention thus makes it possible to avoid prefabricating plates of gel before performing electrophoresis, thus achieving a considerable saving in time, means, and effort.

The invention also improves the quality of the results obtained insofar as electrophoresis takes place in a medium that is more uniform because there are no longer any cassettes supporting plates of gel, thereby increasing reliability and reproducibility of macromolecular separation and transfer.

In a first embodiment of the invention, the membranes for placing in the vessel are mounted on frames for support and manipulation purposes, and they are optionally lightly tensioned on the frames.

The frames serve solely to support and tension the membranes, and are much simpler and more compact than in the prior art where the frames were used for making and supporting plates of gel.

In addition, their use facilitates membrane manipulation.

In another embodiment of the invention, the membranes to be placed in the vessel form a continuous strip that is guided along a zigzag path over parallel rollers.

This further reduces and simplifies membrane manipulation both before and after electrophoresis.

The gel used in the present invention is a gel (typically agarose) that can be solidified and liquefied by varying temperature and/or concentration.

The invention also provides a multiple electrophoresis apparatus for controlled migration of macromolecules and for transferring them onto membranes, the apparatus comprising a vessel containing a plurality of parallel elongate electrodes and having means for applying electrical potentials to the electrodes to create between them successively a first electric field for macromolecule migration and separation, and then a second electric field perpendicular to the first for transferring the macromolecules onto the membranes, the apparatus being characterized in that it also comprises:

- means for guiding or supporting the membranes in the vessel parallel to one another and to the above-specified electrodes;
- means for filling the vessel with electrophoresis gel in the liquid phase;
- means for solidifying the gel in the vessel; and
- means for liquefying, dissolving, or decomposing the gel in the vessel.

The means for liquefying the gel are of the type that raises temperature, by heating the vessel and/or heating the electrodes, and/or by causing a hot liquid to circulate in microporous tubes containing the electrodes.

The means for dissolving or decomposing the gel may, for example, be of the type that injects liquid under pressure, or of the suction type, or else of the ultrasound generator type.

In a first embodiment of this apparatus, the membranes are fixed by their edges to support frames which optionally include means for tensioning the membranes.

In a variant embodiment of the apparatus, the membranes form a continuous strip that is guided along a zigzag path over rollers that are substantially parallel to the electrodes.

Advantageously, the rollers for guiding the continuous strip are carried by a common support and form a moving unitary assembly that can be inserted into the vessel and removed therefrom.

The invention will be better understood and other characteristics, details, and advantages thereof will appear more clearly on reading the following description given by way of example and with reference to the accompanying drawings, in which.

Figure 3:
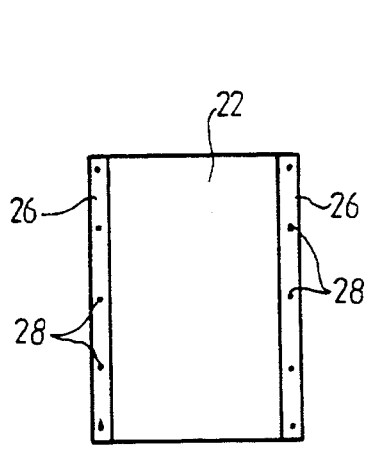
Figure 4:
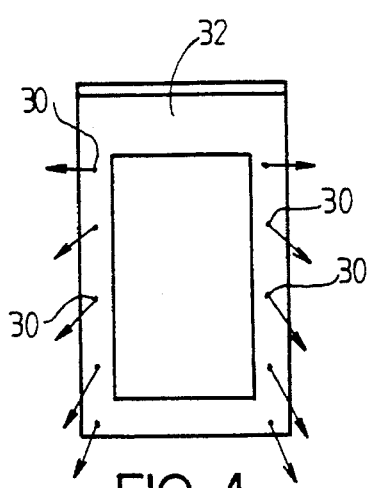
Figure 5:
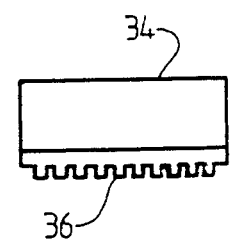

FIGS. 3, 4, and 5 are diagrammatic views of a membrane, a support frame, and a well-forming comb;

FIG. 6 is a diagrammatic view in vertical section through a variant embodiment of the apparatus of the invention;

FIG. 7 is a diagrammatic elevation view of a membrane support and guide assembly, usable in the FIG. 6 apparatus; and FIG. 8 is a fragmentary diagrammatic plan view of the FIG. 7 assembly.

Reference is made initially to FIGS. 1 to 5 which are diagrams of a first embodiment of apparatus of the invention.

Figure 1:
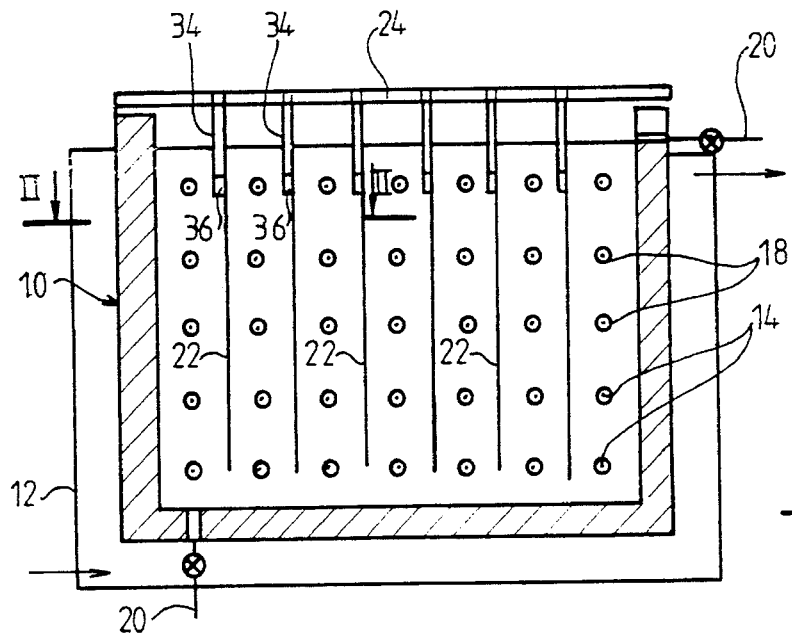
FIG. 1 is a diagrammatic vertical section view of electrophoresis apparatus of the invention.
Figure 2:
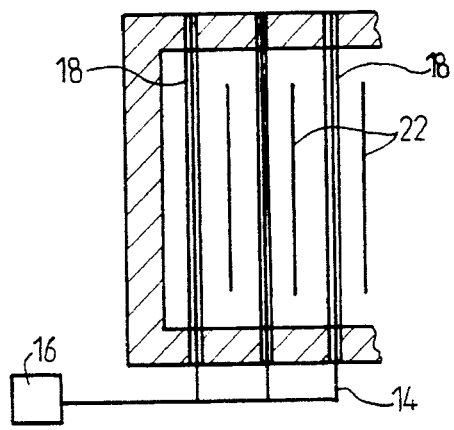
FIG. 2 is a fragmentary diagrammatic view in horizontal section on line II—II of the FIG. 1 apparatus.

In FIG. 1, there can be seen an electrophoresis vessel 10 that is substantially in the form of a rectangular parallelepiped, surrounded by a jacket 12 through which a heat-conveying liquid circulates at a temperature that can be regulated for the purpose of heating and cooling the vessel 10.

As described in the Applicant's international application WO 90/02601, the vessel preferably includes a plurality of elongate electrodes 14 which are horizontal and parallel to one another, and which are organized in rows and in columns to form a square-mesh array. The electrodes are constituted by electrically-conductive metal wires and they are connected at their ends (FIG. 2) to means 16 for applying electrical potentials so as to form electric fields extending vertically or horizontally between the rows or between the columns of electrodes.

In the embodiment shown in FIG. 1, the electrodes 14 are housed in small tubes 18 of microporous material which form bubble traps and which may also be used for circulating an appropriate electrolyte.

The vessel 10 also includes electrolyte filling and circulation means which are represented diagrammatically in the form of two ducts 20 each including opening and closing means such as a solenoid valve, one provided on the bottom of the vessel 10 or in the vicinity of its bottom, and the other at the top of the vessel.

According to the invention, these ducts 20 are used to fill the vessel with an electrophoresis gel in liquid form, e.g. an agarose solution at a temperature of the order of 50° C. to 60° C., approx. When the vessel 10 is filled with the agarose solution, the gel is solidified, either by allowing it to cool to ambient temperature, or by accelerating the cooling by causing cold liquid to circulated in the jacket 12, or else by causing cold electrolyte to circulate in the tubes 18 surrounding the electrodes 14, or indeed by connecting the ends of the electrodes 14 to a cold source (the electrodes 14 are generally made of platinum, which is a very good conductor of heat).

In a variant, it is also possible to increase the concentration of the agarose in the solution filling the vessel 10.

The vessel 10 then contains a large block of gel which can be used for migration and separation of macromolecules, samples of which have been deposited in wells formed in the top portion of the block of gel.

Naturally, it is necessary to place membranes of conventional type in the vessel between the columns of electrodes, before proceeding with solidification of the gel.

The simplest method of proceeding is doubtless to place vertical membranes 22 in the vessel between the rows of electrodes, the membranes 22 being, for example, fixed to a support 24 via their top horizontal edges, and being weighted down at their bottom horizontal edges. Thereafter the vessel 10 is filled slowly from the bottom or the top, avoiding eddies, so that the membranes remain as vertical as possible, after which the gel is caused to solidify.

To make the membranes easier to manipulate, and also to guarantee that they are plane when they are impregnated with gel in the liquid phase, it is preferable to mount them on rigid support frames, proceeding essentially in the manner described in the Applicant's international application WO 90/02601 and as shown diagrammatically in FIGS. 3 and 4. Under such circumstances, two extensible strips 26 are initially stuck or welded to the two longitudinal edges of a membrane 22, the strips including holes or orifices 28 for fixing on pegs 30 that are guided to move along the longitudinal edges of a frame 32 in the directions indicated by the arrows. The pegs are urged resiliently outwards relative to the frame by springs so as to keep the membrane 22 under light tension. The tension serves to guarantee that the membrane 22 is plane and to take up any stretching therein, due to impregnation by the liquid gel.

A strip 34 that includes a comb 36 along one of its edges can be engaged on the frame 32 so that the comb 36 extends substantially along the top horizontal edge of the membrane 22 so as to form, later on, wells in the gel for receiving samples of macromolecules.

The apparatus of the invention is then used as follows:

Initially the membranes 22 are prepared by fixing the extensible strips 26 along their edges, and then placing the membranes 22 on the frames, and finally installing the strips 34 that carry the combs 36.

Thereafter, the frames 32 together with the membranes 32 and the combs 36 are placed in the vessel as shown in FIG. 1, with the vessel being filled with gel in the liquid phase either before or after the frames 32 and the membranes 22 are installed, after which the gel is caused to solidify by cooling and/or increasing its concentration of gelling agent.

Once the gel has solidified, the strips 34 carrying the combs 36 are withdrawn and samples of macromolecules are deposited in the rows of wells that are formed in the gel along the horizontal top edges of the membranes 22. Different electrical potentials are then applied to the rows of electrodes 14 to create vertical electric fields between the rows of electrodes, thereby causing the macromolecules contained in the above-mentioned wells to move vertically through the gel towards the bottom of the vessel 10.

After a certain amount of time, during which the macromolecules travel distances through the gel that are a function of their molecular masses, the distribution of electrical potentials at the electrodes 14 is altered so as to apply different potentials to the columns of electrodes, thereby establishing electric fields between them that are horizontal and perpendicular to the membranes 22. Under the effect of these electric fields, the macromolecules move horizontally through the gel and become fixed on the membranes.

Thereafter, the gel is liquefied, dissolved, or decomposed.

This can be done by raising the temperature of the gel, by causing hot water to flow in the jacket 12 surrounding the vessel 10. It can also be done by causing hot electrolyte to flow along the tubes 18 containing the electrodes 14. It is also possible to inject a hot liquid under pressure into the vessel 10 to decompose the gel, or to dissolve it by injecting an appropriate enzymatical liquid solution (e.g. an agarose solution for an agarose gel).

In a variant, it is also possible to close the vessel 10 in leakproof manner and establishes a partial vacuum therein, thereby causing water to evaporate from the gel and thereby decompose the gel.

It is also possible to apply mechanical or ultrasound vibration to the gel, thereby detaching the gel from the membranes and/or decomposing it more or less completely.

Once the gel has been liquefied, dissolved, decomposed, or merely unstuck from the membranes, the frames 32 are extracted from the vessel, the membranes 22 are removed therefrom, and then processed in conventional manner.

Thereafter, it is necessary to empty the vessel completely and to wash it before filling it with a new gel in the liquid phase to perform a new electrophoresis operation.

In the variant embodiment shown diagrammatically in FIGS. 6 to 8, the membranes form a continuous strip 40 which is guided over top and bottom horizontal rollers 42 and 44 mounted to rotate freely about horizontal axes that are parallel to the electrodes 14 of the vessel. The top rollers 42 are above the electrodes 14 and the maximum level of gel in the vessel, while the bottom rollers 44 are preferably below the bottom row of electrodes 14. The strip 40 constituting the membranes passes alternatively over a top roller 42, then a bottom roller 44, and then another top roller 42, etc. so as to form vertical lengths of membrane between successive columns of electrodes 14.

The rollers 42 and 44 are preferably carried by a common support, e.g. comprising a top frame 46 that carries the axle of the rollers 42, and vertical legs 48 attached to the top frame 46 and carrying the axles of the bottom rollers 44. This common support is advantageously movable so as to be capable of being extracted from the vessel 10 in order to position a continuous strip of membrane 40 over the rollers 42 and 44, and then be lowered into the vessel 10 for electrophoresis. The axles of at least some of the top rollers 42 may be associated with return springs 50 as shown diagrammatically in FIG. 7 so that the rollers 44 are urged continuously upwards in order to exert a small amount of tension on the strip 40 that is plunged in the vessel.

Otherwise, the apparatus can be identical to that described with reference to FIGS. 1 to 5.

It is used as follows:

With the support of the rollers 42 and 44 withdrawn from the vessel, a strip 40 is initially put into place over the rollers.

Simultaneously, the vessel 10 may be filled with gel in liquid form, after which the roller support is lowered slowly into the vessel. Conversely, it would also be possible to place the support inside the vessel before filling it slowly with gel in liquid form.

Once the lengths of membrane have been completely immersed in the gel, combs 34, 36 are placed between the top rollers 42 as shown diagrammatically in FIG. 6. Like the rollers 42 and 44, the combs may be carried by a common support.

Thereafter the gel is caused to solidify, using the means as described above.

The combs are then removed and samples of macromolecules are deposited in the wells formed in the gel by the teeth of the combs. Thereafter it suffices to apply the desired potential differences to the electrodes 14 in order firstly to cause the macromolecules to migrate and to become separated by moving vertically downwards, and then to cause the macromolecules to be transferred horizontally onto the vertical lengths of membrane.

The gel is then liquefied, dissolved, or decomposed using the same means as those described above.

Thereafter the support for the rollers 42 and 44 can be removed from the vessel and traction can be applied to one end of the strip so as to recover the lengths of membrane onto which the macromolecules have been transferred.

Simultaneously, new lengths of membrane for use in the following electrophoresis operation are brought into place between the rollers 42 and 44.

During this time, the vessel 10 is emptied and cleaned and readied for a new electrophoresis operation.

In a variant embodiment (not shown), the rollers for guiding the strip 40 may be vertical. In this case, it is preferable for the electrodes in the vessel to be vertical likewise, so as to avoid excessively complicating the placing of the lengths of strip between the planes of electrodes.

The continuous strip 40 which forms the lengths of membrane between the planes of electrodes can be constituted by a long length of membrane providing the membrane is mechanically strong enough. However, when the mechanical characteristics of the membrane are weak, because of its thinness or its material, it is preferable to fix predetermined lengths of membrane over windows previously cut out in a support strip, which may be made out of the same material as the membrane but of greater thickness, or else out of a different material.

We claim:

1. A multiple electrophoresis method for controlled migration of macromolecules and transfer thereof onto membranes in a vessel containing a plurality of parallel elongate electrodes and having means for applying electrical potentials to the electrodes for establishing between them successively a first electric field for macromolecule migration, and then a second electric field perpendicular to the first for transferring the macromolecules onto the membranes, the method comprising placing in the vessel membranes which are parallel to one another and to the electrodes and which extend between the electrodes, and filling the vessel with an electrophoresis gel in the liquid phase, the filling being performed before or after the membranes have been placed in the vessel, then solidifying the gel, subsequently placing samples of macromolecules in wells formed in the gel along one of the edges of the membranes, applying electrical potentials to the electrodes initially to cause the macromolecules to migrate through the gel, and then to transfer them onto the membranes, then liquefying, dissolving, or decomposing the gel, and removing the membranes from the vessel.

2. A method according to claim 1, further comprising emptying and cleaning the vessel before a new electrophoresis operation.

3. A method according to claim 1 wherein the membranes to be placed in the vessel are previously mounted on support and manipulation frames, and are optionally tensioned on said frames.

4. A method according to claim 1 wherein the membranes to be placed in the vessel form a continuous strip that is guided along a zigzag path over parallel rollers.

5. A method according to claim 1 comprising heating or cooling the gel in the vessel by means of the above-specified electrodes.

6. A method according to claim 1 wherein the electrodes are received in microporous tubes and the method comprises causing a hot or cold liquid electrolyte to circulate along said tubes to heat or cool the electrophoresis gel.

7. A method according to claim 1 comprising surrounding the vessel in a jacket for circulating a heat transfer liquid for heating and cooling the electrophoresis gel.

8. A method according to claim 1 comprising dissolving the gel in the vessel by injecting an appropriate enzymatical solution or in decomposing it by applying suction, by injecting liquid under pressure, or by mechanical or ultrasound vibration.

9. Multiple electrophoresis apparatus for controlled migration of macromolecules and for transferring them onto membranes, the apparatus comprising a vessel containing a plurality of parallel elongate electrodes and having means for applying electrical potentials to the electrodes to create between them successively a first electric field for macromolecule migration and separation, and then a second electric field perpendicular to the first for transferring the macromolecules onto the membranes, the apparatus also comprising means for guiding or supporting the membranes in the vessel parallel to one another and to the above-specified electrodes;

means for filling the vessel with electrophoresis gel in the liquid phase;

means for solidifying the gel in the vessel; and means for liquefying, dissolving, or decomposing the gel in the vessel.

10. Apparatus according to claim 9, including means for forming rows of wells in the gel to receive samples of macromolecules.

11. Apparatus according to claim 9 wherein the means for liquefying the gel in the vessel are of the type that raise temperature, by heating the vessel and/or heating the electrodes and/or causing a hot liquid to circulate along microporous tubes containing the electrodes, and/or in a jacket surrounding the vessel.

12. Apparatus according to claim 9 wherein means for dissolving or decomposing the gel are of a type comprising injecting a liquid under pressure, or applying suction, or generating mechanical or ultrasound vibrations.

13. Apparatus according to claim 9 wherein the membranes are fixed by their edges on support frames optionally including means for tensioning the membranes.

14. Apparatus according to claim 9 wherein the membranes form a continuous strip that is guided along a zigzag path over rollers parallel to the electrodes.

15. Apparatus according to claim 14, wherein the rollers for guiding said strip are carried by a common support, together forming a moving unitary assembly that can be inserted in the vessel and extracted therefrom.

16. Multiple electrophoresis apparatus for controlled migration of macromolecules and for transferring them onto membranes, the apparatus comprising a vessel containing a plurality of parallel elongate electrodes and having means for applying electrical potentials to the electrodes to create between them successively a first electric field for macromolecule migration and separation, and then a second electric field perpendicular to the first for transferring the macromolecules onto the membranes, the apparatus also comprising means for guiding or supporting the membranes in the vessel parallel to one another and to the above-specified electrodes, wherein the membranes form a continuous strip and the means for guiding or supporting the membranes includes rollers parallel to the electrodes for guiding the strip along a zigzag path, and wherein the rollers for guiding said strip are carried by a common support, together forming a moving unitary assembly that can be inserted in the vessel and extracted therefrom;

means for filling the vessel with electrophoresis gel in the liquid phase;

means for solidifying the gel in the vessel; and means for liquefying, dissolving, or decomposing the gel in the vessel.

* * * * *

UNITED STATES PATENT AND TRADEMARK OFFICE
CERTIFICATE OF CORRECTION

PATENT NO. : 5,593,561
DATED : January 14, 1997
INVENTOR(S) : Dominique Cognard et al.

It is certified that error appears in the above-identified patent and that said Letters Patent is hereby corrected as shown below:

On the cover page, Section [56] References Cited:

Under "U.S. Patent Documents" the following references should be listed:

| | | |
|---|---|---|
| 4,631,122 | 12/1986 | Pohl |
| 5,293,703 | 3/1994 | Coste et al. |

Under "Foreign Patent Documents" the following references should be listed:

| | | |
|---|---|---|
| 02195249 | 8/1990 | Japan |
| WO92/10272 | 6/1992 | WIPO |

Signed and Sealed this

Twenty-ninth Day of April, 1997

Attest:

*Attesting Officer*

BRUCE LEHMAN

*Commissioner of Patents and Trademarks*